United States Patent [19]

Leyden

[11] Patent Number: 5,036,204

[45] Date of Patent: Jul. 30, 1991

[54] CONTINUOUS CONCENTRATION MONITORING BY CIRCULAR DICHROISM

[75] Inventor: Donald E. Leyden, Chester, Va.

[73] Assignee: Philip Morris, Inc., New York, N.Y.

[21] Appl. No.: 383,717

[22] Filed: Jul. 24, 1989

[51] Int. Cl.$^5$ ............................................. G01N 21/21
[52] U.S. Cl. ................................... 250/373; 250/343; 356/364
[58] Field of Search ................ 250/343, 373; 356/368, 356/367, 366, 364, 373

[56] References Cited

U.S. PATENT DOCUMENTS

| | | | |
|---|---|---|---|
| 2,976,764 | 3/1961 | Hyde et al. | 356/367 |
| 3,257,894 | 6/1966 | Grosjean | 356/368 |
| 3,283,645 | 11/1966 | Wada | 356/364 |
| 3,345,907 | 10/1967 | Wada | 356/323 |
| 3,442,592 | 5/1969 | Grosjean | 356/327 |
| 3,446,557 | 5/1969 | Wilkinson | 356/325 |
| 3,450,478 | 6/1969 | Sebestyen | 356/365 |
| 3,471,240 | 10/1969 | Grosjean | 356/368 |
| 3,540,827 | 11/1970 | Badoz et al. | 356/365 |
| 3,586,443 | 6/1971 | Hooper | 356/365 |
| 3,602,597 | 8/1971 | Sproul | 356/368 |
| 3,612,688 | 10/1971 | Liskowitz | 356/342 |
| 3,632,216 | 1/1972 | Cary | 356/365 |
| 3,637,311 | 1/1972 | Tipotsch | 356/365 |
| 3,741,660 | 6/1973 | Abu-Shumays et al. | 356/364 |
| 4,523,847 | 6/1985 | Bjorklund et al. | 356/349 |
| 4,588,893 | 5/1986 | Vidrine | 250/428 |

FOREIGN PATENT DOCUMENTS

| | | | |
|---|---|---|---|
| 01791989 | 2/1986 | European Pat. Off. | 250/373 |
| 0323699 | 11/1988 | European Pat. Off. | |
| 1209772 | 1/1966 | Fed. Rep. of Germany | 250/373 |
| 2362388 | 3/1978 | France | 356/364 |
| 63-115031 | 5/1988 | Japan | |
| 374971 | 7/1975 | U.S.S.R. | 356/368 |
| 485367 | 12/1975 | U.S.S.R. | 356/368 |

OTHER PUBLICATIONS

Atkinson, W. M., et al., "Determination of Nicotine in Tobacco by Circular Dichroism Spectropolarimetry", Analytical Chemistry, vol. 56, No. 11, Sep. 1984, pp. 1947-1950.

Choat, T. et al., "Variable Path Length Flow-Through Cell for Spectrophotometry Analytical Chemistry", vol. 58, 1986, pp. 2570-2571.

Drake, A. F., et al., "Polarization modulation—the measurement of linear and circular dichroism", Journal of Physics E. Scentific Instruments, vol. 19, 1986, pp. 170-173.

Purdie, N. et al., "Analytical Applications of Polarimetry, Optical Rotatory Dispersion, and Circular Dichroism", Analytical Chemistry, vol. 61, No. 2, Jan. 15, 1989, pp. 77A-89A.

Bowen, John M., et al., "Determination of Cocaine by Circular Dichroism", Anal. Chem. vol. 53, No. 14, (Dec. 1981), pp. 2237-2239.

Schnepp, O., et al., "The Measurement of Circular Dichroism in the Vacuum Ultraviolet", Review of Scientific Instruments, vol. 41, No. 8, (Aug. 1970), pp. 1136-1141.

Galanov, E. K., et al., "Spectropolarization Instrument for Studying Circular Dichroism and Calibration of This Instrument", Sov. J. Opt. Technol., vol. 48, No. 3 (Mar. 1981), pp. 157-160.

Primary Examiner—Constantine Hannaher
Attorney, Agent, or Firm—Eric R. Hubbard

[57] ABSTRACT

Circularly polarized monochromatic electromagnetic radiation of a wavelength correlating the maximum absorbance of a sample compound is directed through a flowing solution containing the sample compound, which exhibits circular dichroism activity, and a plurality of other compounds. Measurement of the circular dichroism effect and comparison of an alternating current signal corresponding to the circular dichroism absorption to a direct current component allows for the constant monitoring of the concentration of the sample compound in the flowing solution. The flowing solution may be under high temperature and pressure and may comprise a supercritical fluid.

13 Claims, 2 Drawing Sheets

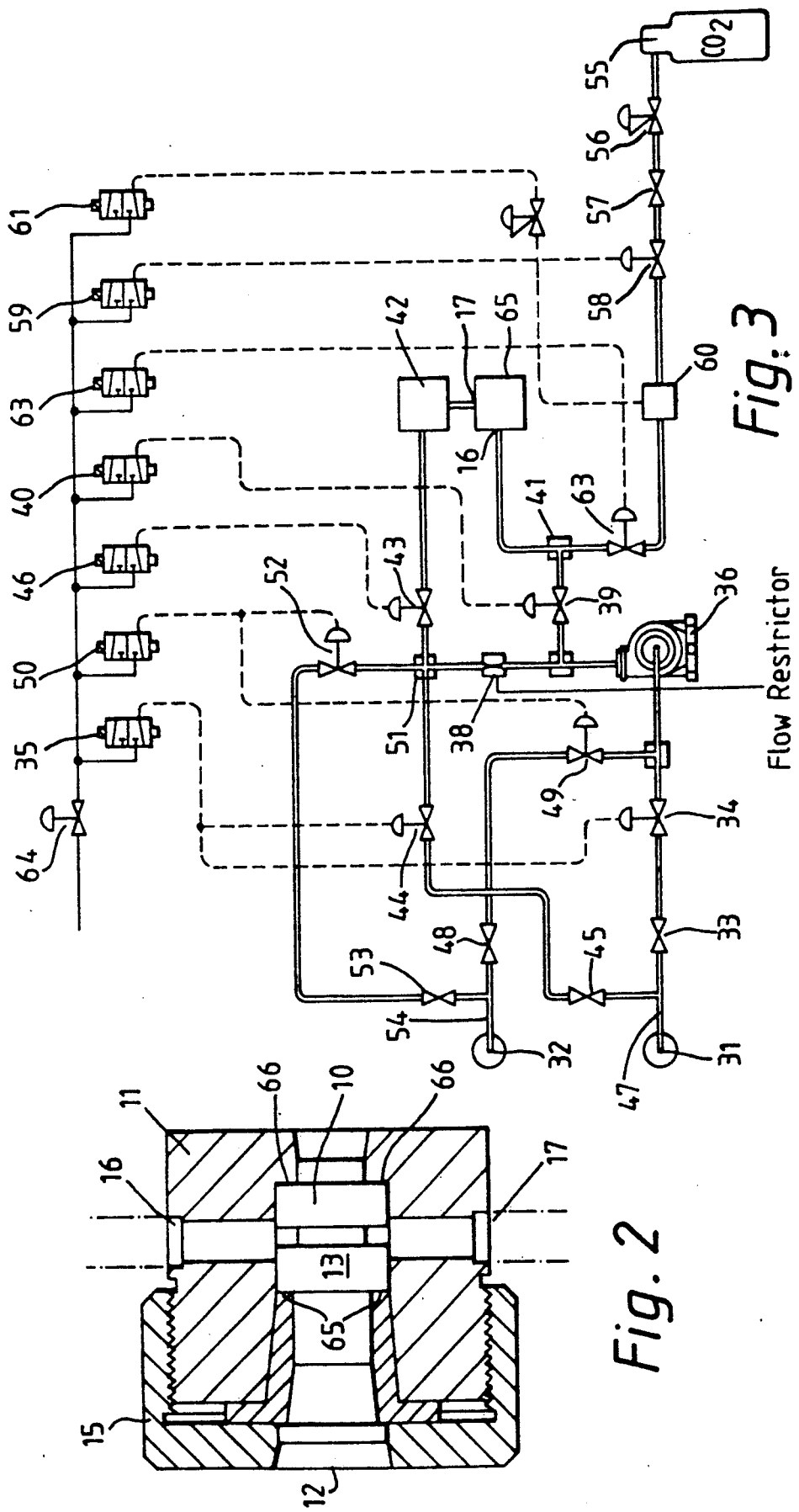

CONTINUOUS CONCENTRATION MONITORING BY CIRCULAR DICHROISM

BACKGROUND OF THE INVENTION

This invention relates to an apparatus and method for continuously monitoring the concentration of a compound which exhibits circular dichroism activity and is contained in a flowing solution also containing a plurality of other compounds in solution.

In industrial processes, it is frequently desired to monitor the concentration of a subject compound which is present in a flowing solution stream containing a plurality of compounds. Further, it is frequently desired that the concentration of the subject compound will be monitored continuously so that the concentration of that compound in the flowing solution stream that is passing the monitor will always be known. The apparatus and method selected for monitoring the concentration of the subject compound depends in part on the chemical or physical characteristics of that compound and in part on the nature and characteristics of the industrial process of which the flowing solution stream is a part.

Depending upon the characteristics of the subject compound, the concentration of that compound might be determined by chemical methods such as high pressure liquid chromatography, gas chromatography, spectrophotometry, or, if the subject compound exhibits circular dichroism activity, by measurement using circular dichroism spectropolarimetry.

Compounds which exhibit circular dichroism activity are those which contain a chiral center in the molecule and which absorb ultraviolet or other electromagnetic radiation. This includes many molecules which are active in biological processes.

As it is presently known to perform circular dichroism spectropolarimetry to monitor the concentration of a compound in a flowing solution, a small volume of sample must first be isolated from the flowing solution stream before analysis of the concentration of the subject compound in a circular dichroism spectropolarimeter can be performed.

A significant problem is that the isolation of the small volume of sample and the execution of the circular dichroism analysis are time consuming and require a significant amount of handling of the sample. Use of more than several minutes to make the concentration determination can negate the effectiveness of the method as a process monitor. This is because the point in the flowing solution stream from which the sample was taken will be too far downstream by the time the concentration of the subject compound in the sample is known. Further, where the flowing solution stream is maintained under extreme conditions of temperature or pressure, isolating a sample is made prohibitively difficult and altering the conditions of the sample to allow for handling can alter or destroy the integrity of the compounds in the sample. Thus, as presently performed, circular dichroism spectropolarimetry apparatus and methods may be prohibited for monitoring the concentration of compounds in some flowing sample streams.

It is, therefore, the object of this invention to provide an apparatus and method for using circular dichroism spectropolarimetry to continuously monitor the concentration of a subject compound which exhibits circular dichroism activity in flowing solution streams without having to remove a sample of the solution from the flowing stream.

It is the further object of this invention to provide an apparatus and method capable of continuously monitoring the concentration of a subject compound in a flowing solution stream where the solution stream is maintained under extreme conditions of temperature and pressure.

SUMMARY OF THE INVENTION

The present invention provides for an apparatus and method for continuously monitoring the concentration of a subject compound which exhibits circular dichroism activity in a flowing solution which contains a plurality of compounds.

The apparatus of the invention includes a generating means for generating a beam of alternately left circularly polarized and right circularly polarized monochromatic electromagnetic radiation. This beam of electromagnetic radiation is directed through a flow cell. The flow cell has a first and a second separate straight channel therethrough, which intersect at a single point along their paths. The flowing solution passes through the first channel and the beam of electromagnetic radiation passes through the second channel such that the beam of electromagnetic radiation must first traverse a first transparent plate, then the flowing solution, and then a second transparent plate before exiting the flow cell. The first and second transparent plates are located to isolate the first channel from the second channel and define the distance the beam of electromagnetic radiation must travel through the flowing solution. The first and second transparent plates must be comprised of a material which has no adverse dichroic effects on the beam of electromagnetic radiation.

Upon exiting from the flow cell, the intensity of the beam of electromagnetic radiation is detected by a means for detecting which converts the intensity measure into an electronic signal containing a direct current component and an alternating current component. The concentration of the subject compound is then found by a means for determining which measures the ratio of the direct current component to the alternating current component. The concentration measure is then recorded by a means for recording.

In a preferred embodiment of the apparatus of the invention, the flow cell can accommodate a flowing solution at a pressure greater than atmospheric.

In another preferred embodiment of the apparatus of the invention, the flow cell can be heated to correspond to the temperature of the flowing solution.

In another preferred embodiment of the apparatus of the invention, the distance between the first and second transparent plate is 2-3 millimeters or as is appropriate for the flowing solution selected.

The method of the present invention includes providing a flowing solution including a subject compound that exhibits circular dichroism activity and directing the flowing solution through a flow cell, generating a beam of alternately left and right circularly polarized electromagnetic radiation in the ultraviolet spectrum of a wavelength corresponding to the maximum circular dichroism absorbance of the subject compound, passing the beam of electromagnetic radiation through the flow cell and the flowing solution, detecting the intensity of the beam of electromagnetic radiation after passage through the flowing solution and converting the intensity measure into an electronic signal comprising a direct current component and an alternating current component, the alternating current component representing the difference of absorption of the left circularly polarized beam and the right circularly polarized beam, and determining the concentration of the subject compound in the flowing solution by measuring the ratio of the alternating current component to the direct current component.

In a preferred embodiment of the method of the invention, the flowing solution is provided at a pressure greater than atmospheric.

In another preferred embodiment of the method of the invention, the flowing solution provided comprises a super critical fluid solution.

In another preferred embodiment of the method of the invention, the subject compound is nicotine and the flowing solution provided comprises a super critical fluid carbon dioxide solution.

In another preferred embodiment of the method of the invention, the subject compound is nicotine and the flowing solution provided comprises extracts from tobacco in super critical fluid carbon dioxide.

BRIEF DESCRIPTION OF THE DRAWINGS

The above and other objects and advantages of the invention will be apparent on consideration of the following detailed description, taken in conjunction with the accompanying drawings, in which like references refer to like parts throughout, and in which:

FIG. 2 is an over-head view of the flow cell in accordance with an embodiment of the present invention.

FIG. 3 is a diagram of a sampling loop which is a part of an industrial process including an embodiment of the present invention.

DETAILED DESCRIPTION OF THE INVENTION

Figure 1:
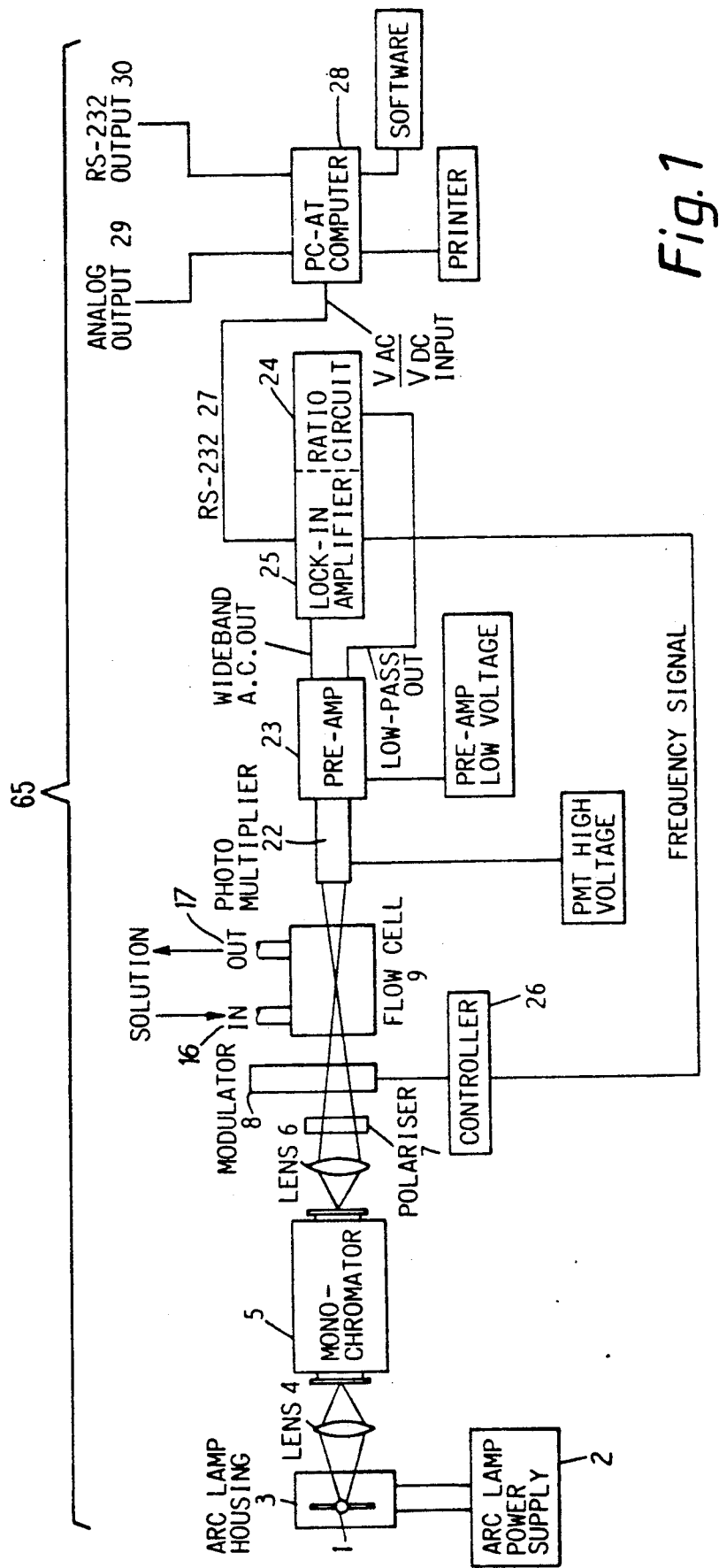
FIG. 1 is a block diagram of a circular dichroism measuring system in accordance with an embodiment of the present invention.

As shown in FIG. 1, an illustrative embodiment of a circular dichroism spectropolarimeter, electromagnetic radiation is generated by ozone-free short gap arc lamp 1, which is commercially available from Optical Radiation Corp., 1300 Optical Drive, Azusa, Calif. 91702, under model number USA-150-7. Arc lamp 1 is powered by arc lamp power supply 2, and resides in arc lamp housing 3. Electromagnetic radiation travels from arc lamp 1, through double convex lens 4, which directs the electromagnetic radiation at monochromator 5.

Monochromator 5 is commercially available from Instruments, S.A., Inc., 6 Olson Avenue, Edison, N.J. 08820, under model number R4315. Monochromator 5 is capable of outputting electromagnetic radiation of a single wavelength over a wide range of wavelengths in the ultraviolet spectrum. This invention is intended to cover the use of this circular dichroism spectropolarimeter and method for its use over the entire wavelength range of monochromator 5. The wavelength selected should correspond with the Wavelength of maximum circular dichroism absorption of a subject compound whose concentration is sought to be monitored. In a preferred embodiment of the invention, monochromator 5 is adjusted to output electromagnetic radiation of 264 nm, the wavelength found to give the maximum circular dichroism absorption for nicotine in a supercritical fluid carbon dioxide solution.

Electromagnetic radiation outputted from monochromator 5 is directed at double convex lens 6, which focuses the radiation on polarizer 7. Polarizor 7 linearly polarizes the monochromatic electromatic radiation and allows it to travel into photoelastic modulator 8.

Photoelastic modulator 8, which is commercially available from Hinds International, Inc., P.O. Box 929, Hillsboro, Oreg. 97123-0929, under model number PEM-80, transforms the monochromatic electromagnetic radiation from being linearly polarized to being alternately left circularly polarized and right circularly polarized. Photoelastic modulator 8 effects this transformation by applying pulses of electric current at a given frequency to a crystaline quartz piezoelectric transducer (not shown) which is within the photoelastic modulator and through which the electromagnetic radiation travels. Application of this current phase-shifts the electromagnetic radiation, resulting in circularly polarized monochromatic radiation which alternates between left rotation and right rotation at a frequency equal to the frequency of the pulses of electric current applied to the piezoelectric transducer.

Alternately left and right circularly polarized monochromatic electromagnetic radiation travels from photoelastic modulator 8 to flow cell 9. Flow cell 9, which is commercially available from Harrick Scientific, Ossining, N.Y. York 10562, model no. HPLC-13, is depicted in FIG. 2. Flow cell 9 is comprised of two opposing transparent quartz plates 10 and 13, which are adjustably mounted in housing 11 so that the circularly polarized electromagnetic radiation entering flow cell 9 through opening 12, passes through quartz plate 13, then travels through the flowing sample solution, then passes through quartz plate 10, and exits the flow cell through exit opening 14. Housing 11 is constructed in such a way that the flow cell 9 is capable of withstanding flowing sample solution pressures of greater than 3500 psi. Flow cell 9 is capable of being heated to the temperature of the flowing solution.

In a preferred embodiment of the invention, the flowing solution is held at a pressure of 3500 psi ($241.325 \times 10^5$ Pa.) and a temperature of 140 deg. F (60 deg. C.).

The distance between quartz plate 13 and quartz plate 10 defines a path length and is adjustable. The path length is fixed by interposition of stainless steel spacer not shown and by movement of collar 15 which secures quartz plate 13. Selection of the path length is important for accurate concentration measure. The path length must be long enough to obtain a measurable absorption of the circularly polarized radiation but not so long that background absorption will distort the measurement. It has been found that the best results are obtained with a pathlength range of 2-3 mm. In a preferred embodiment of the invention, the pathlength is 3 mm.

Housing 11 is constructed to allow passage of the flowing sample solution. The solution is allowed to travel between opening 16 and opening 17, passing through housing 11, then between quartz plates 13 and 10 and through the beam of electromagnetic radiation, then through housing 11 before exiting.

Quartz plates 13 and 10 are each sealed to prevent leakage of the flowing sample solution by O-ring seals 65 and 66, respectively. Where the subject compound is nicotine in a flowing sample solution comprising extracts from tobacco and super critical fluid carbon dioxide it is critical that O-ring seals 65 and 66 be made of an ethylene/propylene copolymer which is commercially available and may be obtained from Parker Seals, O-ring Division, 2360 Palumbo Drive, Lexington, Kentucky 40509, under model number E0962-90 to maintain the seal.

Referring to FIG. 3, the flowing sample solution can be monitored at either of two points along the path of a sample stream, extractor port 31 or absorber port 32. When it is desired to determine the concentration of the subject compound at extractor port 31, the flowing sample solution enters that port and travels through blocking valve 33, which is manually controlled. The sample solution then travels through air-actuated valve 34, which is controlled by three-way valve 35. From air-actuated valve 34, the sample solution travels into pump 36.

Pump 36 directs the sample solution to t-joint 37. At t-joint 37 some of the sample solution will be directed to flow cell 9 and some will be directed back to the sample stream without having its concentration determined. The volume of sample solution directed toward the flow cell is controlled by flow restrictor 38. Flow restrictor 38 is important to the operation of the sample loop because it allows regulation of the pressure added to the sample solution in the sampling loop. It is desirable that this pressure change be minimal without effecting flow through the sample loop.

From t-joint 37, the sample solution travels through air-actuated valve 39 which is controlled by 3-way valve 40 and past t-joint 41 and into opening 16.

After passing through flow cell 9, the sample solution travels through opening 17 and past flow meter 42 which measures the volume of the sample solution passing it per unit time. The sample solution then passes through air-activated valves 43 and 44 which are controlled by 3-way valves 46 and 35, respectively. After traveling through blocking valve 45, the sample solution is returned to the flowing sample stream through exit passage 47 which surrounds extractor port 31.

If it is desired to determine the concentration of the subject compound at absorber port 32, the sample solution enters the sample loop at that port and passes through blocking valve 48 before passing through air-actuated valve 49, which is controlled by 3-way valve 50. The sample solution then travels into pump 36. From pump 36, the sample solution from absorber port 32 follows the same route as sample solution from extractor port 31 until it reaches intersection 51.

At intersection 51, the sample solution from absorber port 32 is directed through air-actuated valve 52, which is controlled by 3-way valve 50. From air-actuated valve 52 the flowing sample passes through blocking valve 53 and back into the flowing sample stream through exit passage 54 which surrounds absorber port 32.

The sample solution is drawn from only one of the sampling ports by concerted action of 3-way valves 35, 40, 46 and 50. When it is desired to sample from extractor port 31, 3-way valves 35, 40 and 46 open air-actuated valves 34, 39, 43 and 44 while 3-way valve 50 keeps air-actuated valves 49 and 52 closed. When it is desired to sample from absorber port 32, 3-way valves 50, 40 and 46 open air-actuated valves 49, 39, 43 and 52 while 3-way valve 35 keeps air-actuated valves 34 and 44 closed.

Flow cell 9 and flow meter 42 can be flushed of impurities precipitated from the sample solution with clean carbon dioxide. Carbon dioxide from reservoir 55 passes through manual shut-off valve 56, blocking valve 57 and air-actuated valve 58, which is controlled by 3-way valve 59, and into booster pump 60. Booster pump 60 propels the carbon dioxide toward opening 16 by the action of air from 3-way valve 61. The carbon dioxide then travels through air-actuated valve 62 which is controlled by 3-way valve 63, through opening 16, flow cell 9, opening 17, and flow meter 42. The carbon dioxide, carrying the impurities flushed from flow cell 9 and flow meter 42, then travels through air-actuated valves 43 and 44 and through blocking valve 45 before exiting into the flowing sample solution through exit passage 47. Alternatively, the carbon dioxide and impurities could travel from air-actuated valve 43 through air-actuated valve 52 and blocking valve 53 before exiting into the flowing solution through exit passage 54.

When the sample loop is being flushed, no sample enters from either extractor port 31 or absorber port 32. This is accomplished by closing air-activated valves 39, 34, 49 and 44 or 52, depending on the desired exit route of the carbon dioxide. Valve closing is accomplished by action of 3-way valves 40, 35, 50 respectively.

3-way valves 35, 50, 46, 40, 63, 59 and 61 control the respective air-activated valves by regulating the flow of air to the air-regulated valves. Manual shut-off valve 64 controls the flow of air to the 3-way valves.

In a preferred embodiment, the flowing sample stream is included in an industrial process as described in pending U.S. patent applications Ser. Nos. 122,760 and 122,761. The flowing solution stream and the sample solution which travels through flow cell 9 contains super critical carbon dioxide at a pressure of 3000–3500 psi (20–24 MPa), and a temperature of about 140 deg. F. (60 deg. C.) and also includes nicotine and other compounds which are extracted from tobacco.

After exiting flow cell 9, the electromagnetic radiation enters photomultiplier 22, which is commercially available from Hamamatsu Corp., 360 Foot Hill Drive, P.O. Box 6910, Bridgewater, N.J. 08807-0910, under model number R4315. Photomultiplier 22 transforms the circularly polarized electromagnetic radiation into a electronic signal with a direct current component and an alternating current component. The direct current component represents radiation which has been partially absorbed by compounds in the flowing solution which do not exhibit circular dichroism activity. The alternating current component represents the difference of absorption of the left circular polarized beam and the right circularly polarized beam by the subject compound which exhibits circular dichroism activity.

The direct current component travels to low voltage pre-amp 23 where the signal is amplified. The amplified direct current component then travels to ratio circuit 24.

The alternating current component travels through low voltage pre-amp 23 to lock-in amplifier 25, which amplifies the alternating current signal. Lock-in amplifier 25 is electronically connected to modulator 8 by controller 26. Controller 26 transmits an electronic signal to lock-in amplifier 25 representative of the frequency of the electric current pulses applied to the piezoelectric transducer of modulator 8. This signal allows lock-in amplifier 25 to more strongly amplify the alternating current signal in the frequency range corresponding to the frequency of the current pulses being applied to the piezoelectric transducer of modulator 8.

The alternating current signal travels from lock-in amplifier 25 to ratio circuit 24. Ratio circuit 24 electronically calculates the ratio of the alternating current signal to the direct current signal.

The alternating current signal, direct current signal and an electronic signal representing the ratio of alternating current to direct current are then transmitted by RS-232 digital channel 27 to digital computer 28.

Digital computer 28 is programmed to be capable of outputting the concentration of the subject compound or data corresponding to the direct current signal or the alternating current signal. This output can be by analog output 29 or by digital output 30.

Thus, a continuous monitor of the concentration of a subject compound in a flowing solution which exhibits circular dichroism and a method for its use are provided. One skilled in the art will appreciate that the present invention can be practiced by other than the described embodiment, which is presented for purposes of illustration and not of limitation, and the present invention is limited only by the claims which follow.

I claim:

1. An apparatus for continuously monitoring the concentration of a subject compound in a flowing solution, comprising:
    means for generating a beam of alternately left circularly polarized and right circularly polarized monochromatic electromagnetic radiation directed along a path;
    a flow cell positioned down said path from the means for generating and having first and second separate straight channels therethrough which intersect at a single point, the first channel being arranged so the flowing solution passed therethrough and the second channel being arranged so that the beam of electromagnetic radiation passes therethrough;
    first and second transparent plates, comprised of a material which has no adverse dichroic effects on the beam of electromagnetic radiation, in said flow cell positioned relative to each other and to said channels so that said beam of electromagnetic radiation traverses said first plate, then said flowing solution, and then said second transparent plate before exiting the flow cell, the first and second transparent plates being located to isolate said first channel from said second channel;
    means for continuously detecting the intensity of said beam of electromagnetic radiation after passage through the flowing solution in said flow cell and converting the intensity measure into an electronic signal comprising a direct current component and an alternating current component;
    means for continuously determining the concentration of the subject compound in the flowing solution by measuring a ratio of the direct current component to the alternating current component to the alternating current component.

2. The apparatus of claim 1, wherein the flow cell can accommodate the flowing solution at a pressure greater than atmospheric.

3. The apparatus of claim 2, wherein the flow cell is constructed to accommodate the flowing solution at a pressure greater than 3000 psi (20 MPa).

4. The apparatus of claim 3, wherein the flow cell is constructed to accommodate a flowing solution comprising super critical carbon dioxide containing nicotine and extracts from tobacco.

5. The apparatus of claim 1, wherein the flow cell is heated.

6. The apparatus of claim 1, wherein the first and second transparent plates of the flow cell are 2-3 millimeters apart.

7. The apparatus of claim 1, further comprising means for continuously recording the concentration of the subject compound.

8. A method for continuously measuring the concentration of a subject compound in a flowing solution, which compound exhibits circular dichroism activity, comprising:
    providing the flowing solution which includes the subject compound;
    directing the flowing solution through a flow cell;
    generating a beam of electromagnetic radiation with a wavelength corresponding to the maximum absorbance by the subject compound which is alternately left circularly polarized and right circularly polarized and which is directed along a path;
    passing the beam of electromagnetic radiation through said flowing solution in said flow cell;
    continuously detecting the intensity of the beam of electromagnetic radiation after passage through the flowing solution in said flow cell and converting the intensity into an electronic signal comprising a direct current component and an alternating current component, the alternating current component representing the difference of absorption of the left circularly polarized beam and the right circularly polarized beam;
    continuously determining the concentration of the subject compound in the flowing solution by measuring the ratio of the alternating current to the direct current component.

9. The method of claim 8 wherein the flowing solution is under high pressure.

10. The method of claim 8, wherein the flowing solution is a super critical fluid.

11. The method of claim 10, wherein the super critical fluid is carbon dioxide.

12. The method of claim 8, wherein the subject compound is nicotine and the flowing solution contains extracts from tobacco in super critical fluid carbon dioxide.

13. The method of claim 8, further comprising the step of continuously recording the concentration of the subject compound in the flowing solution.

* * * * *